United States Patent [19]

Doenges et al.

[11] Patent Number: 4,756,015
[45] Date of Patent: Jul. 5, 1988

[54] X-RAY SCANNER

[75] Inventors: Gerhard Doenges, Heidenrod; Cornelius Koch, Wiesbaden, both of Fed. Rep. of Germany

[73] Assignee: Heimann GmbH, Fed. Rep. of Germany

[21] Appl. No.: 57,317

[22] Filed: Jun. 4, 1987

[30] Foreign Application Priority Data

Jul. 14, 1986 [DE] Fed. Rep. of Germany ....... 3623722

[51] Int. Cl.$^4$ ............................................. G01N 23/04
[52] U.S. Cl. ........................................ 378/57; 378/58; 378/99; 378/146
[58] Field of Search ................... 378/99, 57, 58, 146; 250/358.1, 359.1, 360.1

[56] References Cited

U.S. PATENT DOCUMENTS 4,178,510 12/1979 Wagner .
4,562,470 12/1985 Dinh et al. ............................ 378/99

Primary Examiner—Carolyn E. Fields
Assistant Examiner—Joseph A. Hynds
Attorney, Agent, or Firm—Hill, Van Santen, Steadman & Simpson

[57] ABSTRACT

An x-ray scanner generates a fan-shaped x-ray beam through which an object to be inspected is moved and a detector line which generates signals corresponding to the radiation attenuated by the object. The processing electronics includes a comparator for recognizing faulty detector signals by means of which the roll-in of data ito the image memory is controllable such that, given a faulty detector signal, the transfer of the information into a memory line allocated to the detector is inhibited. The x-ray scanner also includes an allocator unit which omits predetermined detector channels for the purpose of geometric balancing. Given outage of a detector, its detector channel is omitted by the allocator unit, based on a signal from the comparator, instead of a prescribed detector channel.

3 Claims, 2 Drawing Sheets

X-RAY SCANNER

BACKGROUND OF THE INVENTION

1. Field of the Invention

The present invention is directed to an x-ray scanner having an x-radiator which generates a fan-shaped x-ray beam at one side of a conveyor means, and a line of individual detectors at the other side of the conveyor means with goods to be inspected being moved through the beam by the conveyor means.

2. Description of the Prior Art

Such scanners are known which include electronics for the acquisition and processing of the detector signals a following viewing means. The electronics includes at least one image storage which having a respective memory row per each individual detector, and a comparator for the recognition of faulty detector signals by means of which the roll-in of data into the image memory is controllable, such that the transfer of the information into the memory row allocated to the detector is inhibited given a faulty detector signal.

X-ray scanners of this type are used, for example, for inspecting luggage. Each of the detectors can be composed of a scintillator for converting x-radiation into visible light which is then converted into an electrical current by a photodiode. For processing the measured values in parallel form, the measured values are converted into a serial sequence of analog measured values via electronic switches (multiplexers), are digitized and are written into a digital image memory such that a running image arises upon display of the storage contents on a video monitor via a digital-to-analog converter. Given a horizontally running image, data are written into the image memory in columns. Every detector then generates a line of the video picture.

An x-ray scanner of this type is known wherein the detector line is bent at a right angle and extends over two sides of the examination space. The location-dependent distortion thereby occurring is eliminated in accord with the teachings of E-A-No. 0 100 562 using an allocator unit which, on the basis of electronically controlled omission of detector channels, equalizes the non-linear scaling function such that the imaging scale corresponds to that of an ideally linear or circular arc-shaped line. In this known x-ray scanner, the perception has been exploited that individual, missing detector channels within the detector row do not lead to a noticeable deterioration of the generated video picture. Permanently prescribed detector channels are thereby omitted.

An individual detector can fail in an x-ray scanner of this type. If the down detector is adjacent to the detector omitted in accord with the program, this would potentially generate a disturbance visible in the pictorial display if the gradient of the gray scale value, i.e., of the signal amplitude, is adequately high at this location.

SUMMARY OF THE INVENTION

It is an object of the present invention to provide an x-ray scanner of the type described above wherein a disturbance in the pictorial representation which is minimally visible ensues given outage of a detector.

This object is achieved in an x-ray scanner constructed in accordance with the principles of the present invention wherein the electronics includes a comparator for the recognition of faulty detector signals by which the roll-in of data into the image memory is controllable such that the transfer of the information into the memory row allocated to the detector is inhibited given a faulty detector signal. Thus faulty detector signals are not visually displayed. The detector channels omitted due to the allocator unit are hardly visible on the monitor picture. The detector channels to be omitted are in fact pre-programmed therein, but when a detector fails or supplies the faulty signal, its signal is omitted instead of a suitable, pre-programmed detector signal, so that the number of omitted channels is not increased.

DESCRIPTION OF THE PREFERRED EMBODIMENTS

Figure 1:
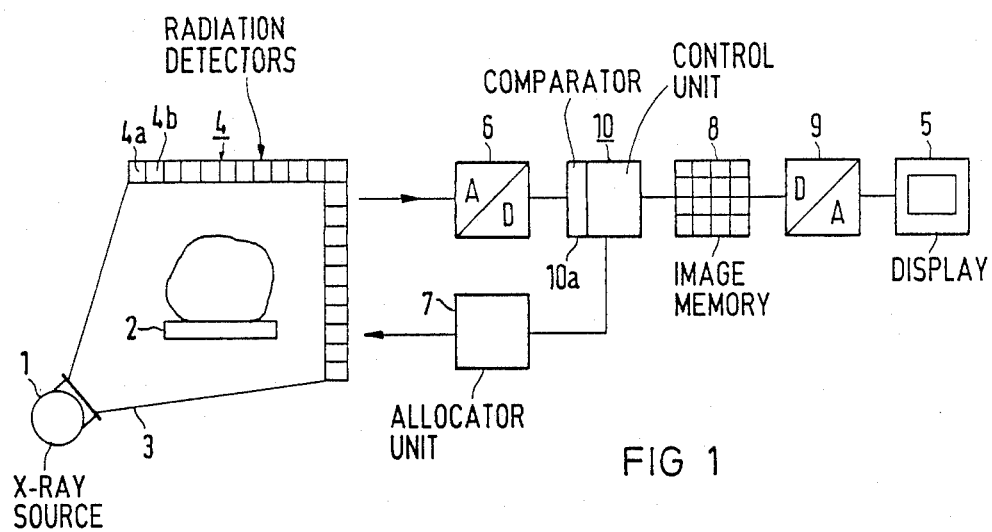
FIG. 1 is a schematic block diagram of an x-ray scanner constructed in accordance with the principles of the present invention.

FIG. 1 shows an x-radiator 1 which transluminates goods on a conveyor means 2 with a fan-shaped x-ray beam 3 whose fan plane lies at a right angle relative to the conveying direction, the conveying direction proceeding perpendicularly to the plane of the drawing. The radiation emerging from the goods is acquired by a line 4 of individual detectors 4a, 4b, etc. bent at a right angle, whose output signals are supplied to a display 5 via processing electronics. The electronics comprises an analog-to-digital converter 6, an allocator unit 7, an image memory 8, a digital-to-analog converter 9, and a control circuit 10 including a comparator 10a.

Figure 2:
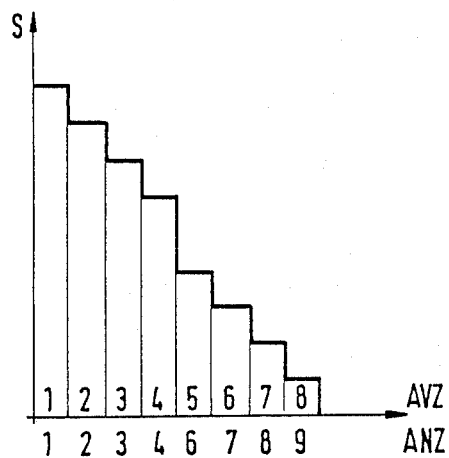
FIGS. 2 through 6 are graphs for explaining the operation of the scanner in FIG. 1.

FIG. 2 shows the curve of the relative signal amplitude S dependent on the addresses preceding and following the allocator unit 7. The address AVZ preceding the allocator unit 7 is thereby shown above the abscissa and the address ANZ following the alloctor unit 7 is thereby shown below the abscissa. This also applies to FIGS. 3 through 6.

In the exemplary signal sequence of FIG. 2, the signal amplitude decreases in steps by the same amount from detector channel to detector channel. It is assumed that the detector line 4 is composed of nine detectors and that the fifth detector is omitted in a programmed fashion, namely for geometric balancing, as disclosed in E-A-No. 0 100 562. Accordingly, the allocator unit 7, coming to the channel 4, forms a signal from the output of channel 5, reduced by two steps, which becomes channel 6 following the allocator unit 7.

Figure 3:
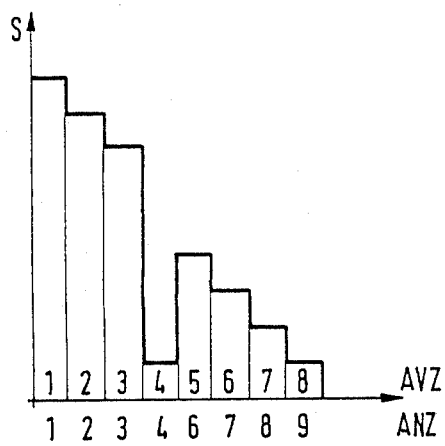

FIG. 3 essentially shows the signal sequence of FIG. 2, however, it has been assumed that the fourth channel is malfunctioning. The comparator 10a recognizes this malfunction by, for example, the exceeding of pre-scribed limit values for the zero signal (offset) and the signal amplitude given 100% x-rate intensity as voltage criteria. Given outage of the fourth channel in accord with FIG. 4, it is then not the fifth channel that the allocator unit 7 omits, but rather channel 4. Channel 3 is thus followed by the originally omitted channel 5 at the channel 4 which again becomes channel 5 following the allocator unit 7.

Figure 5:
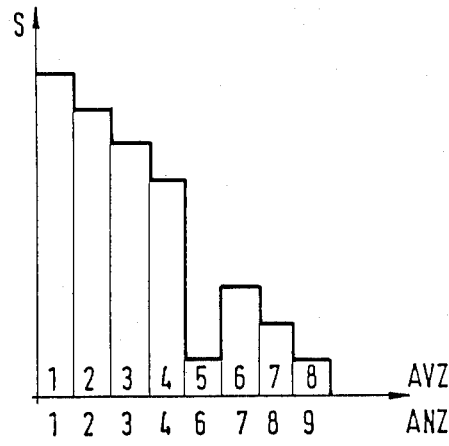
Figure 4:
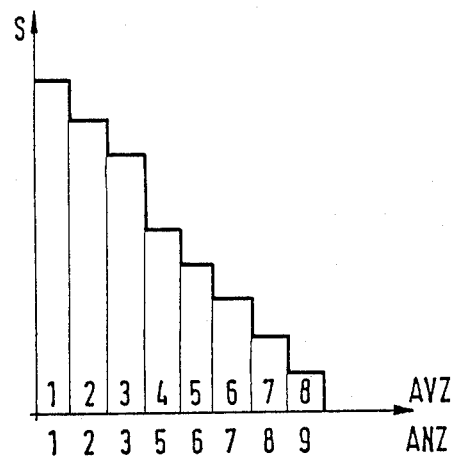
Figure 6:
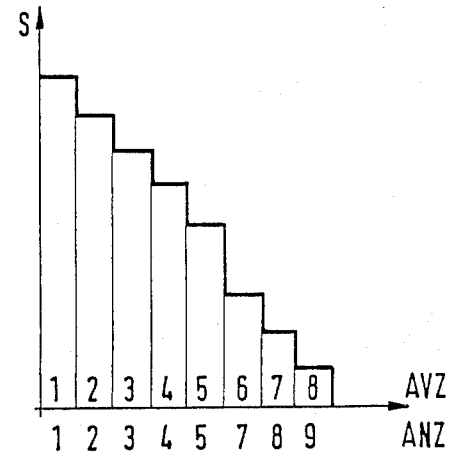

FIG. 5 assumes that the original channel 6, which has become channel 5 due to the omission of original channel 5, is malfunctioning. The comparator 10a likewise recognizes this and causes channel 6 instead of the original channel 5 to be omitted. The original channel 4 is therefore followed by the original channel 5, whereas the original channel 6 is omitted and the original channel 7 becomes channel 6, etc. The channel sequence indicated in FIG. 6 then results following the allocator unit 7.

In the allocator unit 7, thus, the addresses of the down channels are compared to the addresses of the prescribed channels to be omitted for geometric balancing. An optimum number of malfunctioning detector signals are suppressed by modification of the balancing matrix on the basis of omission. Trials have shown that it is permissible to shift the address of an omitted channel by half the distance to the next, omitted channel without the geometric balancing being visibly deteriorated. After the modification has been carried out, the allocator unit 7 is loaded with the corrected addresses by a processor in the allocator unit 7, which contains a write-read memory for this purpose. Trials have further shown that the number of faults that can be suppressed is approximately the same as the number of detector channels omitted for the geometric balancing.

In the example, line 4 was addressed via the allocator unit 7. Omitted detector channels are not addressed and are thus not selected. The comparator 10a detects faults in the way set forth and inhibits the forwarding of data of malfunctioning channels to the image memory 8. Further, the rated addresses for line 4 are generated in the control circuit 10 and the allocator unit 7, which contains a write-read memory, is loaded with the actual addresses needed for geometric balancing and for fault suppression as data.

The invention is not limited to the angled detector of FIG. 1. Given linear lines, individual detector channels can likewise be omitted at regular intervals and, in the malfunction case, malfunctioning channels can be omitted instead of the intended detector channels.

Although modifications and changes may be suggested by those skilled in the art it is the intention of the inventors to embody within the patent warranted hereon all changes and modifications as reasonably and properly come within the scope of their contribution to the art.

We claim as our invention:

1. An x-ray scanner comprising:
an x-ray source which generates a fan-shaped x-ray beam;
a conveyor means for moving an article to be examined through said fan-shaped x-ray beam;
a plurality of detector channels each having a detector which detects radiation attenuated by said article and generates an electronic signal corresponding to the attenuated radiation incident on the detector;
an image memory connected to said detector channels having a respective memory location for each of said detectors respectively in said channels; and
means for controlling entry of data from said detector channels into said image memory by transferring said data from said detector channels into said image memory with transfer from predetermined detector channels being inhibited comparator means for recognizing one or more of said electronic signals as a faulty detector signal, and upon recognition of a faulty detector signal by said comparator means said means for controlling inhibiting transfer of data from the channel having the faulty detector signal instead of inhibiting one of said pre-determined detector channels.

2. A method for operating an x-ray scanner comprising the steps of:
moving an article to be inspected through a fan-shaped x-ray beam;
detecting the radiation attenuated by said article using a plurality of detectors which generate respective electronic signals as an output in respective detector channels corresponding to the attenuated radiation incident on the respective detectors;
normally transferring data from said detector channels into an image memory with transfer from pre-determined detector channels being inhibited to geometrically balance the outputs of said detectors;
identifying one or more of said electronic signals as a faulty detector signal; and
upon the identification of a faulty detector signal, inhibiting transfer of data from the channel having the faulty detector signal instead of inhibiting transfer of data from one of said pre-determined detector channels.

3. An x-ray scanner comprising:
an x-ray source which generates a fan-shaped x-ray beam;
conveyor means for moving an article to be inspected through said fan-shaped x-ray beam;
a plurality of detectors disposed for receiving radiation attenuated by said article, each of said detectors generating an electronic signal as an output in an associated detector channel corresponding to the attenuated radiation incident on the respective detectors;
an analog-to-digital converter connected to each of said detector channels which converts the signals in each of said channels to respective digital signals;
an image memory;
a control unit means for controlling entry of data from each of said channels from the analog-to-digital converter into said image memory, said control unit means including a comparator which recognizes faulty detector signals;
an allocator unit means connected to each of said detector channels and to said control unit means for inhibiting transfer of data from selected channels by said control unit means into said image memory to geometrically balance the outputs of said detectors and, upon identification of a faulty detector signal by said comparator, for inhibiting transfer of data from a channel having said faulty detector signal instead of inhibiting transfer of data from one of said pre-determined detector channels; and
means connected to said image memory for constructing and displaying a visual image of said article from the contents of said image memory.

* * * * *